(12) United States Patent
Caizza (10) Patent No.: US 11,207,469 B1
(45) Date of Patent: Dec. 28, 2021

(54) LOW DEADSPACE SYRINGE INCLUDING A PIVOTING NEEDLE GUARD

(71) Applicant: Expressions Design Studio, LLC, Union City, NJ (US)

(72) Inventor: Richard Caizza, Union City, NJ (US)

(73) Assignee: Expressions Design Studio, LLC, Union City, NJ (US)

( * ) Notice: Subject to any disclaimer, the term of this patent is extended or adjusted under 35 U.S.C. 154(b) by 0 days.

(21) Appl. No.: 17/192,481

(22) Filed: Mar. 4, 2021

(51) Int. Cl.
*A61M 5/32* (2006.01)
*A61M 5/31* (2006.01)
*A61M 5/34* (2006.01)
*A61M 5/50* (2006.01)

(52) U.S. Cl.
CPC ........ *A61M 5/3216* (2013.01); *A61M 5/3129* (2013.01); *A61M 5/3293* (2013.01); *A61M 5/348* (2013.01); *A61M 5/5066* (2013.01); *A61M 2205/581* (2013.01); *A61M 2205/582* (2013.01)

(58) Field of Classification Search
CPC .............. A61M 5/3216; A61M 5/5066; A61M 5/3293; A61M 5/348; A61M 5/3129; A61M 2205/582; A61M 2205/581
See application file for complete search history.

(56) References Cited

U.S. PATENT DOCUMENTS

| | | | |
|---|---|---|---|
| 4,973,310 A * | 11/1990 | Kosinski | A61M 5/5013 604/110 |
| 4,982,842 A | 1/1991 | Hollister | |
| 5,232,455 A | 8/1993 | Hollister | |
| 5,584,817 A * | 12/1996 | van den Haak | A61M 5/322 604/110 |
| 5,599,313 A * | 2/1997 | Gyure | A61M 5/3216 604/111 |
| 5,662,617 A * | 9/1997 | Odell | A61M 5/3216 128/919 |
| 5,669,889 A | 9/1997 | Gyure et al. | |
| 5,807,351 A | 9/1998 | Kashmer | |
| 6,582,397 B2 | 6/2003 | Alesi et al. | |
| 6,719,737 B2 | 4/2004 | Kobayashi | |
| 7,220,249 B2 | 5/2007 | Hwang et al. | |
| 7,250,038 B2 | 7/2007 | Simpson et al. | |
| 7,537,581 B2 | 5/2009 | Hwang | |
| 7,648,480 B2 | 1/2010 | Bosel et al. | |
| 7,722,572 B2 | 5/2010 | Sprinkle et al. | |
| 7,854,723 B2 | 12/2010 | Hwang et al. | |
| 7,967,794 B2 | 6/2011 | Bosel et al. | |
| 8,226,604 B2 | 7/2012 | Madin et al. | |
| 8,414,560 B2 | 4/2013 | Bush et al. | |
| 8,622,960 B2 | 1/2014 | Madin et al. | |
| 9,205,205 B2 | 12/2015 | Burns et al. | |
| 2001/0041866 A1 * | 11/2001 | Capes | A61M 5/50 604/110 |
| 2002/0072715 A1 | 6/2002 | Newby et al. | |
| 2004/0176722 A1 * | 9/2004 | Capes | A61M 5/5066 604/110 |

(Continued)

FOREIGN PATENT DOCUMENTS

EP   0925083 B1   12/2003

*Primary Examiner* — Amber R Stiles
(74) *Attorney, Agent, or Firm* — Budzyn IP Law, LLC (57) ABSTRACT

A low deadspace syringe having a pivoting protective needle guard on a fixed needle assembly that is permanently attached to the syringe.

19 Claims, 8 Drawing Sheets

(56) References Cited

U.S. PATENT DOCUMENTS

| | | | |
|---|---|---|---|
| 2005/0065482 A1* | 3/2005 | Hauri | A61M 5/3202 604/263 |
| 2005/0124944 A1 | 6/2005 | Hwang | |
| 2007/0208311 A1* | 9/2007 | Farrar | A61M 5/343 604/187 |
| 2011/0092952 A1* | 4/2011 | Voellmicke | A61M 5/008 604/506 |

* cited by examiner

(PRIOR ART)

FIG 7

(PRIOR ART)

FIG 8

(PRIOR ART)

Normal Length Syringe

Optimal Length Syringe

LOW DEADSPACE SYRINGE INCLUDING A PIVOTING NEEDLE GUARD

FIELD OF THE INVENTION

Figure 1:
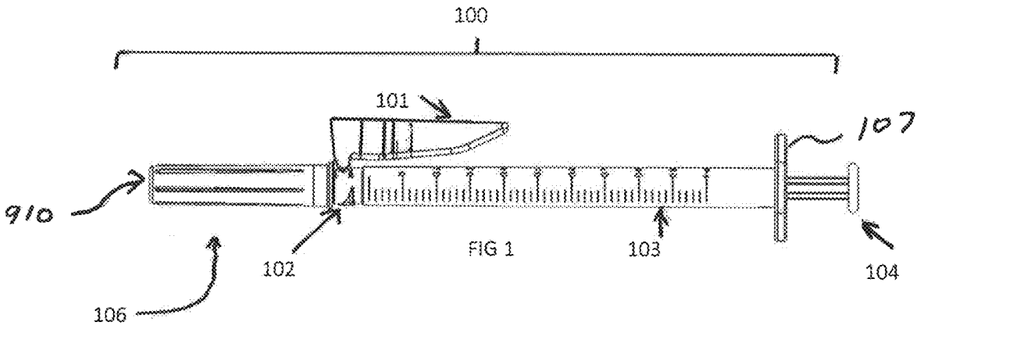
FIG. 1 is a side elevation view of a low deadspace syringe with a pivoting protective needle guard on a permanently attached fixed needle assembly in accordance with the subject invention.

This invention relates to a low deadspace syringe having a pivoting protective needle guard on a fixed needle assembly that is permanently attached to the syringe, as shown, for example, in FIG. 1.

BACKGROUND OF THE INVENTION

Figure 2A:
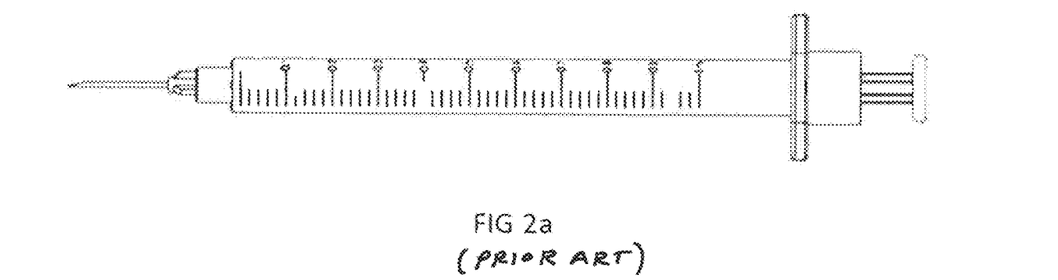
FIGS. 2a-2b are a side elevation and cross-sectional views of an existing insulin syringe with a uni-body fixed needle integrally molded hub.
Figure 2B:
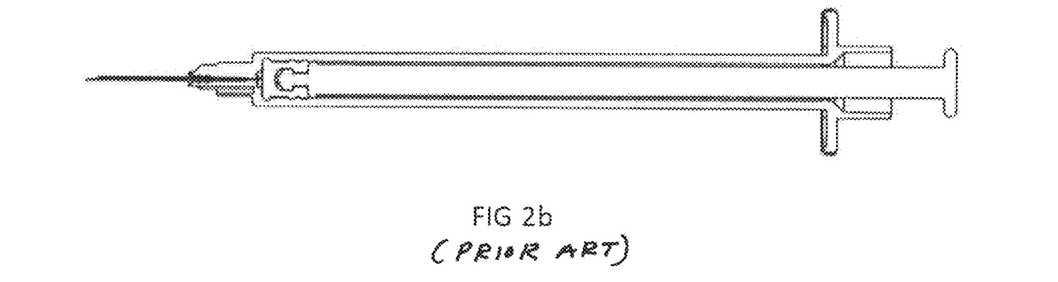
Figure 3A:
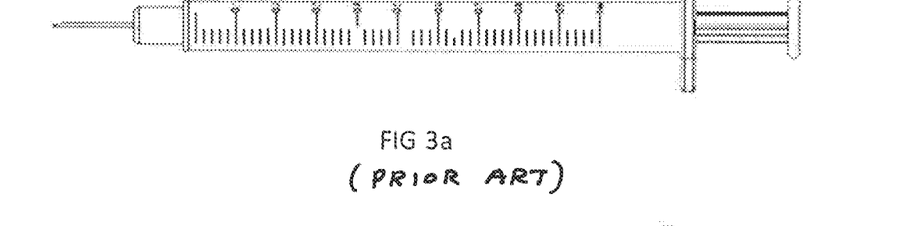
FIGS. 3a-3b are a side elevation and cross-sectional views of an existing insulin syringe with a fixed needle having a molded syringe barrel that is permanently fitted with a separately molded hub.
Figure 3B:
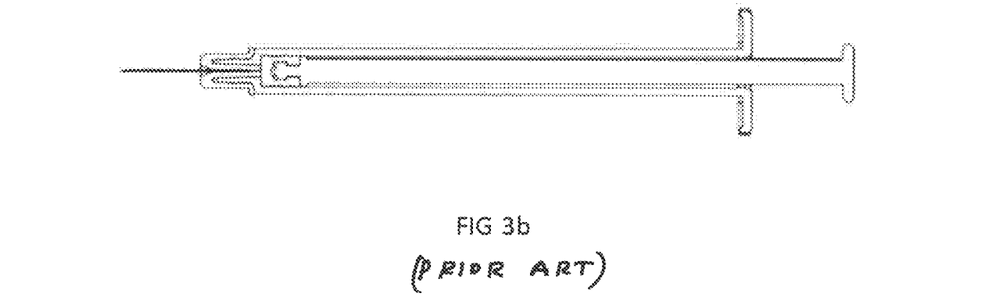

Low deadspace (LDS) syringes with uni-body fixed needle (FN) integrally molded hubs (FIGS. 2a-2b) are widely utilized within the healthcare community most commonly for insulin or vaccination syringes where dosages are small (<1 ml) and medication is limited and expensive. Another two-piece version of a low deadspace (LDS) syringe with a fixed needle (FN) has a molded syringe barrel that is permanently fitted with a separately molded hub in manufacturing (FIGS. 3a-3b). A major benefit of these FN syringes is the reduction or near elimination of dead-space which results in medication savings.

Figure 4:
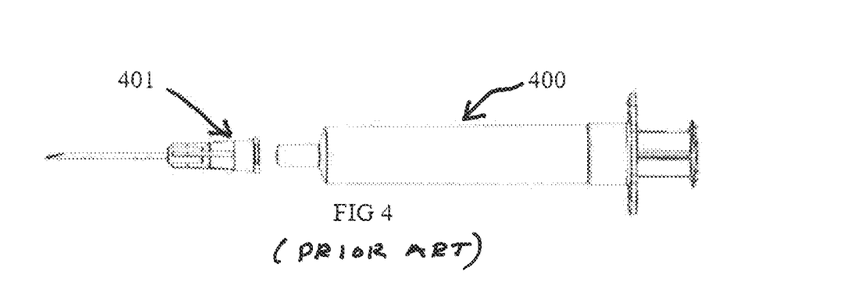
FIG. 4 is a side elevation assembly view of a traditional syringe with a Luer detachable type needle hub assembly.
Figure 5:
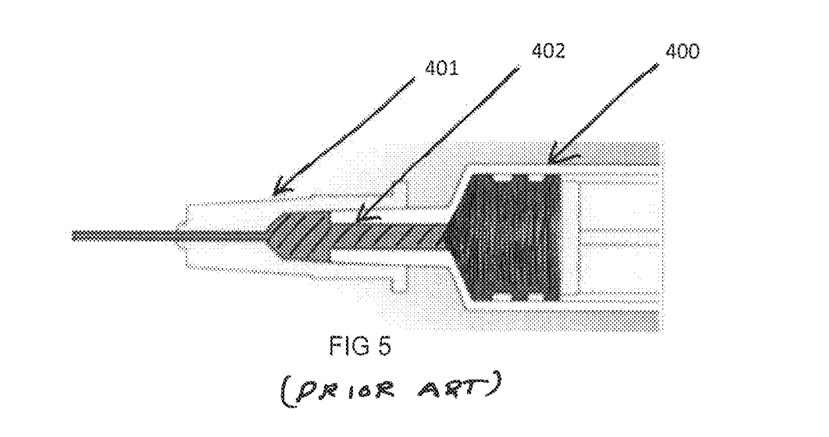
FIG. 5 is an enlarged cross-sectional view of the distal end of the Luer needle hub assembly attached to the syringe shown in FIG. 4 and showing wasted medication contained in deadspace.

Other traditional molded syringes 400 and needles 401 include Luer 6% taper detachable types as shown by example in FIG. 4 syringe barrels can come with a locking threaded collar to securely hold needle. Due to industry design requirement specifications for Luer 6% taper medical connectors like these, a wide range of dimensions for both the needle and syringe exist. These design specifications intentionally leave space between the mating male (typically the syringe) and female (typically the needle hub) parts to ensure that they mate properly. Other contributing factors are in plastic manufacturing where molding the female Luer hub requires additional space beyond the Luer sealing surface adding to a larger space. All this cumulated space between the syringe tip and needle lumen along with the internal hole at the tip of the syringe permits medication to be trapped and leftover after an injection, as shown in the shaded area 402 in FIG. 5 which leads to precious wasted medication.

Figure 6:
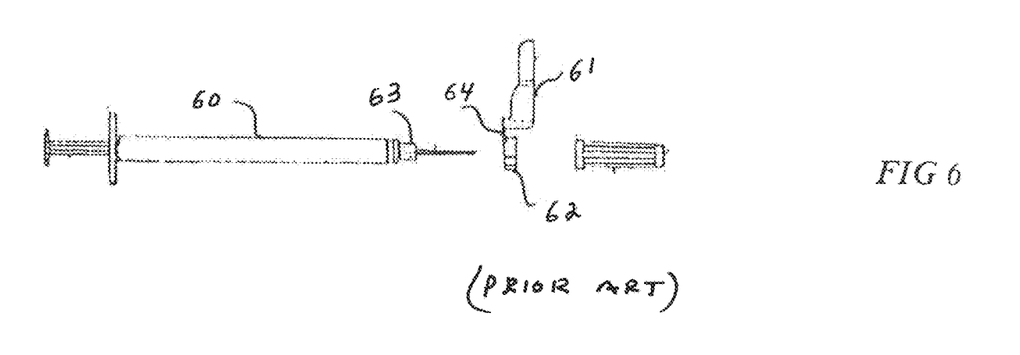
FIG. 6 is an exploded side view of an existing fixed needle syringe receiving an annular ring having a needle guard attached by a living hinge.
Figure 7:
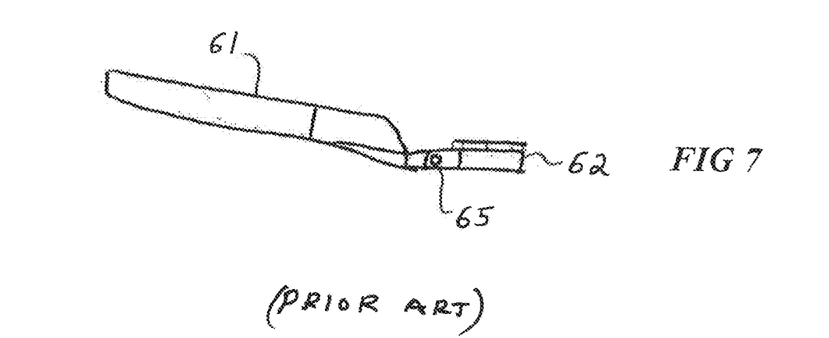
FIG. 7 is a side view of an annular ring with other provisions for attaching a needle guard.
Figure 8:
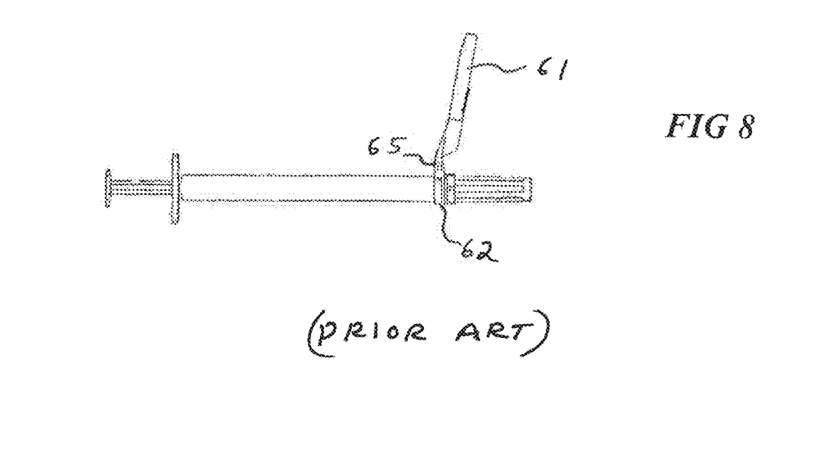
FIG. 8 is an assembled side view of an existing fixed needle syringe with the annular ring and needle guard shown in FIG. 7 attached thereto.

Another type of syringe used today includes a needle guard 61 pivotably attached to an annual ring 62 that is press-fit onto the distal end 63 of a unibody type syringe 60. The annular ring 62 may have the needle guard 61 integrally molded thereto with a living hinge 64 as described in U.S. Pat. No. 7,648,480 (FIG. 6) or have provisions 65 for attaching the needle guard 61 as shown in U.S. Pat. No. 7,722,572 (FIGS. 7-8). In all these cases the technology is limited due to the plastic materials used in both the annular ring and mating syringe body. The nature of plastic materials is that when two mating parts are force fit together the hoop stresses that are created will cause the material in either or both parts to creep until a point of relaxation. When the plastic relaxes (which may take only hours or a couple of months) the parts no longer will have a desired tight fitment and can easily be moved or rotated relative to one another even inadvertently during activation of the needle guard. Adding more interference by making one of the parts smaller or larger only increases the stresses which can accelerate the relaxation hence reducing the desired fit. Other factors that can come into play with press-fit annular ring technology is heat and radiation, these too will have effects on the interference fit and relaxation between the mating parts allows them to creep and move as the designs allow unrestrained movement in some directions (collapsing or expanding).

The above-mentioned patents adapt annular ring technology to uni-body type syringes that have a hub integrally molded at the distal end of the syringe barrel with a needle bonded into the hub prior to attaching the needle guard. An additional shortcoming of this type of design occurs when assembling the needle guard to the completed syringe during manufacturing which may result in the annular ring damaging the sharp needle point when passing over the sharp needle point. In this case, the entire syringe and needle guard would need to be discarded which is costly and adds to the waste cycle negatively impacting the environment.

As mentioned, force fitting the annular ring technology can also result in the needle guard being loosely attached to the syringe which may result in the needle guard spinning while the user is attempting to activate the needle guard. Such movement can lead to a safety issue with potentially dire consequences if the user is accidentally pricked with the used contaminated needle during the shielding process. Balancing of forces with this type of technology is difficult to control when attempting to have the annular ring tight enough to resist rotation when being activating but loose enough to rotate when the user wants to rotate the guard in order to orientate the guard with the bevel point of the needle for some procedures.

Needle pop-off is another serious safety issue that can be caused by interchangeable needles that have not been properly secured (having a connection force between needle hub and syringe tip greater than the activating force) to the syringe barrel tip. Such needles may be inadvertently dislodged when a user attempts to activate a needle guard since the direction of the force to activate the needle guard is in the same direction for removal of the mounted needle from the syringe tip. The current invention is directed to a permanently factory attached hub syringe connection that removes this concern.

SUMMARY OF THE INVENTION

Exemplary embodiments of the current invention address at least the above problems and/or disadvantages and provide at least the advantages described below. The current invention relates to a low deadspace syringe having a pivoting protective needle guard on a fixed needle assembly that is permanently attached to the syringe.

In one exemplary embodiment, a low deadspace syringe assembly comprises a syringe barrel having a chamber for retaining fluid and an open distal end having a coupling extending therefrom that is connected to a distal wall opening in the chamber and a needle assembly having a hub, a cannula and a guard rotatably mounted on the hub to rotate from an open position to a locked safety position, wherein the guard covers the distal end of the cannula when in the locked safety position, and the proximal end of the hub having a cork extending therefrom and into the coupling of the syringe barrel to connect a conduit in the hub to the chamber such that the proximal end of the conduit is substantially flush with the distal wall opening in the chamber. With such a configuration deadspace in the syringe is minimized while still providing a pivoting protective needle guard on the fixed needle assembly permanently attached to the syringe barrel.

As used herein, the term "distal," and derivatives thereof, shall refer to a direction towards a patient, while the term "proximal," and derivatives thereof, shall refer to a direction away from a patient. Also note that other objects, advantages and salient features of the current invention will become apparent to those skilled in the art from the flowing detailed description of exemplary embodiments of the invention taken in conjunction with the referenced drawings.

BRIEF DESCRIPTION OF THE DRAWINGS

The invention will be more fully understood from the following detailed description, in conjunction with the following figures, where.

DETAILED DESCRIPTION OF THE INVENTION

Referring to FIG. 1, a low dead-space fixed needle syringe 100 includes a permanently attached, separately molded needle assembly 106 having a hub 102 with an attached pivoting protective needle guard 101. Syringe dead-space is the volume of residual fluid that remains within the syringe assembly after the plunger 104 is fully depressed during a medication injection. A low dead-space fixed needle syringe can result in a reduction in wasted medication 30 times that of a traditional detachable Luer taper syringe 400 with a mating Luer taper hub 401. As shown in FIG. 1 needle hub 102 of needle assembly 106 is preferably attached to the syringe barrel 103 of the syringe 100 with a press-fit fluid seal interference fit. Hub 102 on needle assembly 106 is preferably made of plastic. However, syringe barrel 103 may be made of glass or plastic and still provide the press-fit fluid seal interference fit.

Figure 9:
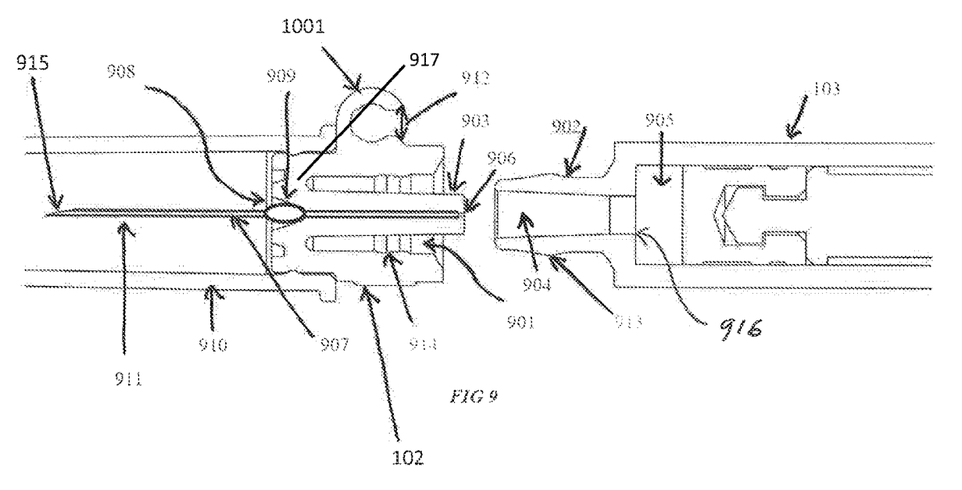
FIG. 9 is an enlarged exploded cross-sectional assembly view of the distal end of the low deadspace syringe and the needle assembly shown in FIG. 1 in accordance with the subject invention.

The needle hub 102 is permanently mounted to the syringe barrel 103 in the manufacturing process. As shown in FIG. 9, needle hub 102 includes a needle cannula 911 extending from its distal end and a needle hub cavity 901 within its proximal end that allows for the barrel nozzle tip 902 to engage and permanently connect with needle hub 102. A sealing cork 903 is included within needle hub cavity 901 and due to sealing cork 903 having an outer diameter larger than the internal orifice 904 of barrel nozzle tip 902 an interference fit creates a fluid seal when sealing cork 903 is mated with internal orifice 904 of barrel nozzle tip 902. The permanent connection of sealing cork 903 with barrel nozzle tip 902 is provided by a locking ring 913 surrounding barrel nozzle tip 902 engaging with a locking trough 914 on an interior surface within needle hub cavity 901 and locking ring 913 also thereby maintains sealing cork 903 in sealing engagement with internal orifice 904. Sealing cork 903 when connected to barrel nozzle tip 902 may occupy all or nearly all the area of the internal orifice 904 and may stop at a distal wall opening 916 of the syringe fluid chamber 905 or even minimally enter the syringe fluid chamber 905 area to eliminate any and all dead-space when mating to a syringe barrel 103. The sealing cork 903 may include a conduit 906 allowing bidirectional access between the syringe barrel 103 internal fluid chamber 905 and a needle lumen 907 within and extending through needle cannula 911. The needle hub 102 distal end includes a bulkhead 917 and a cavity 908 for permanently affixing needle cannula 911 typically with an adhesive bonding material 909. A needle protection cap 910 is removably mounted to the distal end of needle hub 102 to protect the sharp bevel point 915 at the distal end of cannula needle 911.

Figure 10:
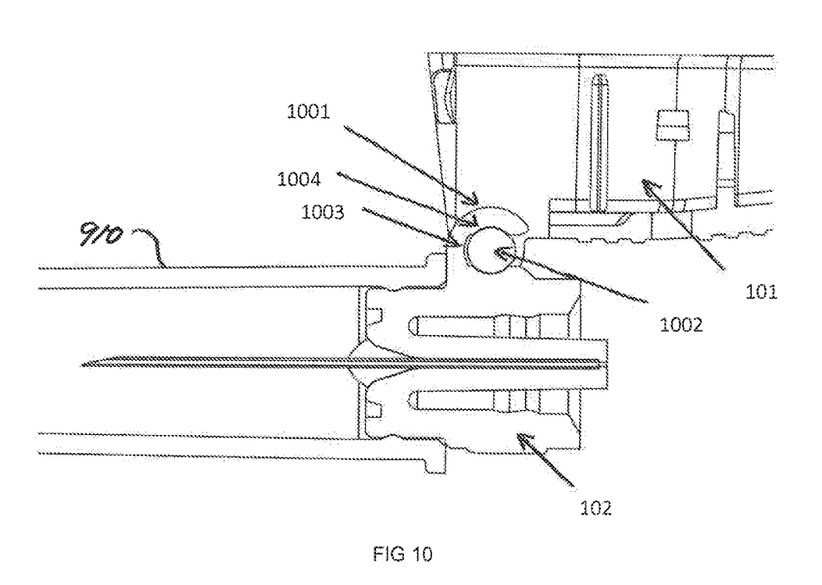
FIG. 10 is an enlarged cross-sectional view of the needle assembly shown in FIGS. 1 and 9 with the needle guard attached thereto in accordance with the subject invention.

As shown in FIG. 10, the invention further includes a needle guard 101 connected and rotatable to the permanently mounted fixed needle hub 102 preferable by the interference gripping fitted C shape clasp 1001 and a clasp opening 912, shown in FIG. 9, that cooperates with a pivot shaft 1002 of needle guard 101. This arrangement permits needle guard 101 easy rotation from an unlocked position, shown in FIGS. 1 and 15, to a final lock position, shown in FIG. 17, before disposal or an alternative intermediate desired position during use. Needle guard 101 can also be connected to fixed needle hub 102 by other known mechanical hinges or an integrally molded living hinge making needle hub 102 and needle guard 101 one molded part. The rotatable fit between needle guard pivot shaft 1002 and C clasp 1001 allows for the user to selectively position the needle guard 101 and maintain an intermediate desired position during a procedure.

Figure 11:
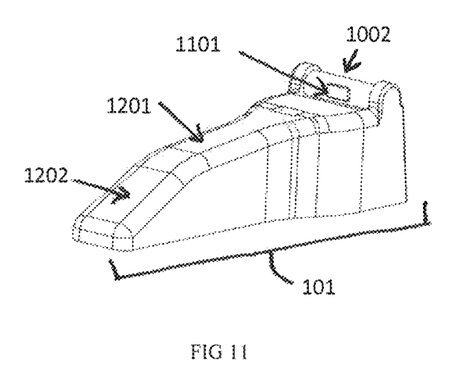
FIG. 11 is a perspective view of a needle guard of the current invention.
Figure 12:
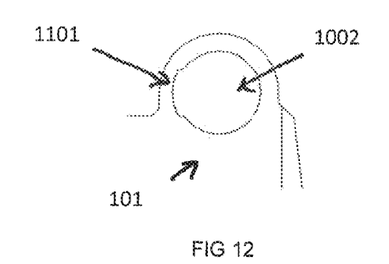
FIG. 12 is an enlarged cross-sectional view of the pivot shaft on the needle guard shown in FIG. 11.
Figure 13:
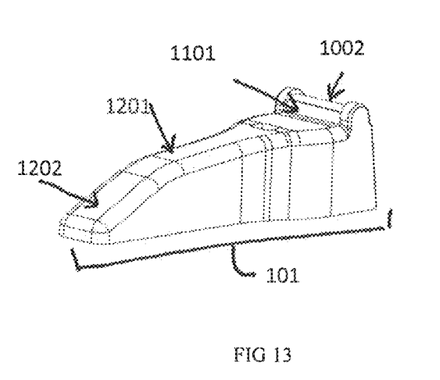
FIG. 13 is a perspective view of an alternative embodiment of a needle guard of the current invention.
Figure 14:
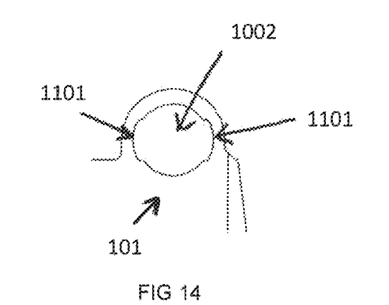
FIG. 14 is an enlarged cross-sectional view of the pivot shaft on the needle guard shown in FIG. 13.

As shown in FIGS. 12 and 14, pivot shaft 1002 of the needle guard 102 includes one or more brakes 1101 that exceed the circumference of the pivot shaft 1002 to intentionally cause friction between pivot shaft 1002 and C clasp 1001. As shown in FIG. 11, brakes 1101 may include a raised area at a concentrated location on pivot shaft 1002 or, as shown in FIG. 13, run the full length of pivot shaft 1002 or something less than the full length. Needle guard 102 is held in its open position when brakes 1101 are positioned in open section 912 of C clasp 1001 and/or in a relief cutout 1003 of the C clasp bearing contact surface 1004, shown in FIG. 10, that the pivot shaft 1002 rides along. Placing the brakes 1101 in an area that does not expose the feature to a compressive load from C clasp 1001 after assembly and before use (shelf life) is advantageous to maintain a desired frictional fit during use. The additional frictional fit between C clasp 1001 and pivot shaft 1002 can be released with the inclusion of a relief area 1003 at the activated mode orientation if desired. Having the frictional feature positioned in the clasp opening 912 or relief 1003 to maintain a stable guard in the packaged position also facilitates the automation of the packaging process.

Figure 15:
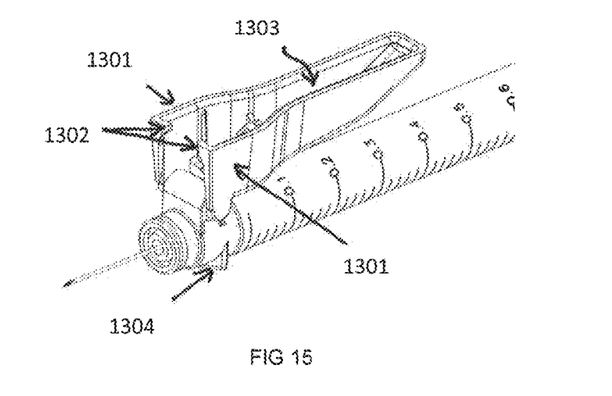
FIG. 15 is a perspective view of the distal end of the low deadspace syringe of the current invention shown in FIG. 1 and its permanently attached fixed needle assembly with the pivoting protective needle guard in an open unlocked position and the needle protection cap removed.
Figure 16:
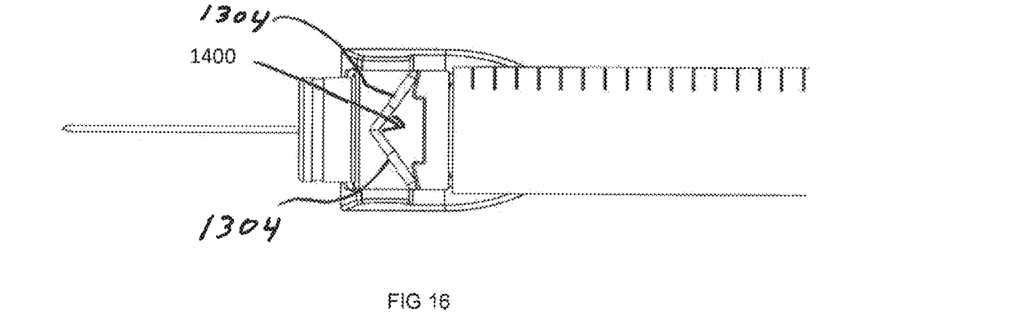
FIG. 16 is a side elevation view of the distal end of the low deadspace syringe of the current invention shown in FIG. 1.

A preferred embodiment of needle guard 101 includes user controlled manual locks activated soon after an injection and before disposal. The user activates the needle guard 101 causing rotation of needle guard 101 over the needle cannula 911 with a force typically by a finger or hard surface. In the preferred embodiment the needle guard 101 includes a one-way secured lock. As shown in FIG. 15, needle guard 101 includes two shielding sidewalls 1301 with two locking tabs 1302, at the end nearest pivot shaft 1002. Each locking tab 1302 extends inward into the needle and hub channel 1303. When the guard 101 is activated the locking tabs 1302 deflect outward when meeting the needle hub ramp 1304 hub lock members, shown in FIG. 16, until they bypass the ramps 1304 and flex back into a position creating a locked unit. As shown in FIG. 16, the hub lock 1400 feature is located on opposite side of needle hub 102 than that of the C clasp 1001. Locking the needle guard 101 to the needle hub 102 may produce an audible sound and tactile feel. The lock is single use. Other locking mechanisms that lock needle guard 101 to the needle hub 102 may be used, e.g., one-way barbed pin into a mating hole.

The preferred embodiment also includes at least one needle hook lock 1501. The needle hook lock 1501 is housed within the needle and hub channel 1303 and may be attached to one side wall 1301 or may extend from a supporting post 1502 mounted on a wall connected to the side walls.

Figure 17:
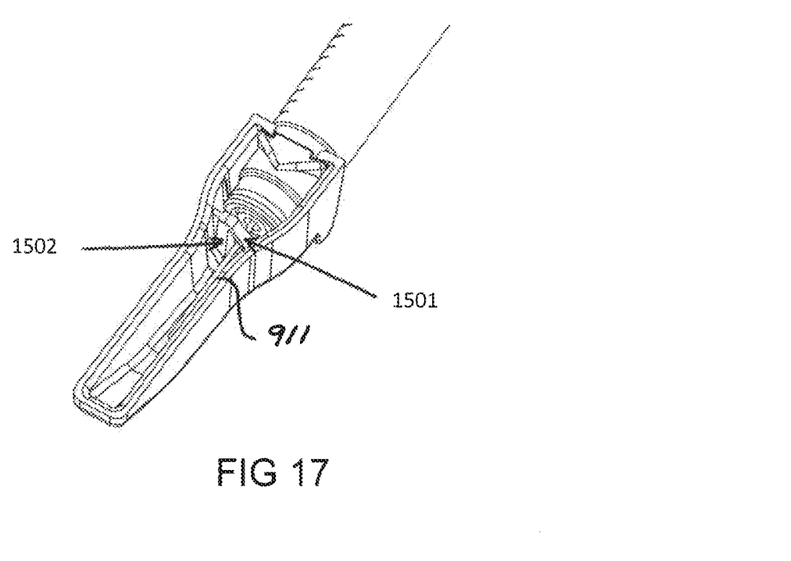
FIG. 17 is a perspective view of the distal end of the low deadspace syringe of the current invention with the pivoting protective needle guard of its fixed needle assembly in a locked safety position.

In the preferred embodiment (hub & needle lock configuration) dual locks engage nearly simultaneously when needle guard 101 is rotated into the desired locked position, as shown in FIG. 17. The needle hook lock 1501 is a narrow deflecting resilient cantilever hook that flexes inward (opposite direction of needle approach) when needle cannula 911 is forced against it allowing the needle cannula 911 to bypass and springs back once needle cannula 911 fully passes by needle hook lock 1501, trapping needle cannula 911 within needle guard 101 which prevents needle cannula 911 from exiting back out. When more than one flexing needle hook lock 1501 is included, the needle locks may be positioned facing one another along the channel. In other embodiments only one (hub or needle) of the two lock systems are included.

As shown in FIGS. 11 and 13, the needle guard cross member wall 1201 that connects the two side walls 1301 includes a finger guiding slanted/curved surface 1202 at the end opposite pivot shaft 1002. When needle guard 101 is at the initial open position needle guard 101 is nearly horizontal to the syringe barrel 103, as shown in FIG. 1, finger guiding slanted/curved surface 1202 allows for user fingertip access between needle guard 101 and syringe barrel 103 to facilitate a one hand activation of needle guard 101 with a substantially horizontal finger stroke.

Figure 18:
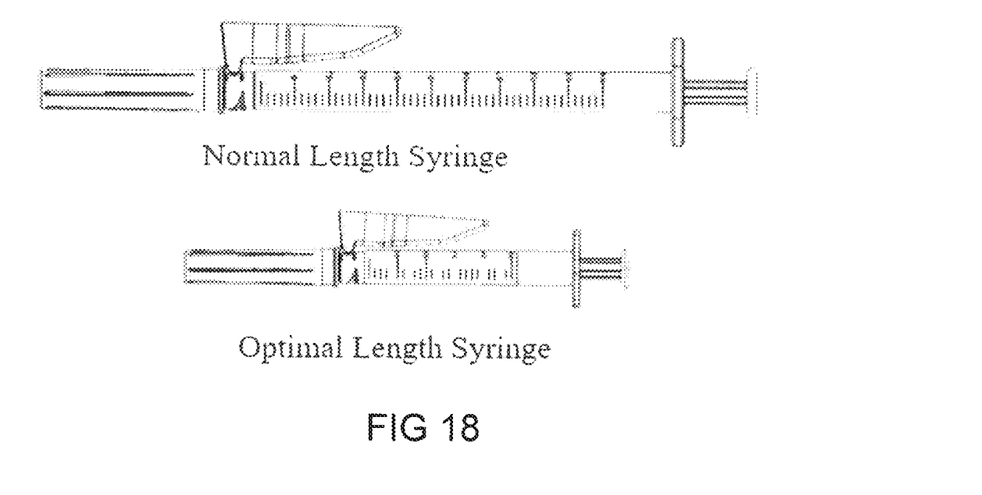
FIG. 18 are side elevation views of low deadspace syringes with pivoting protective needle guards on permanently attached fixed needle assemblies having a normal length syringe barrel and an optimal length syringe barrel in accordance with the subject invention.
Figure 19:
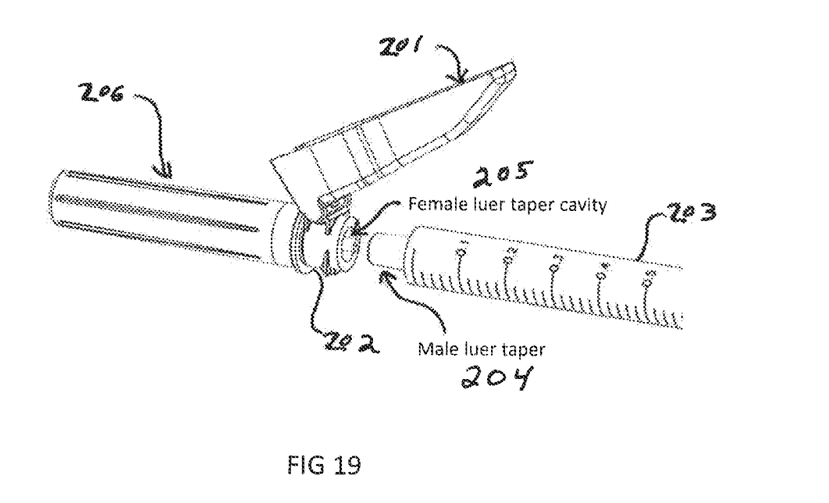
FIG. 19 is a perspective view of a Luer taper syringe and another embodiment of a safety needle assembly of the current invention.
Figure 20:
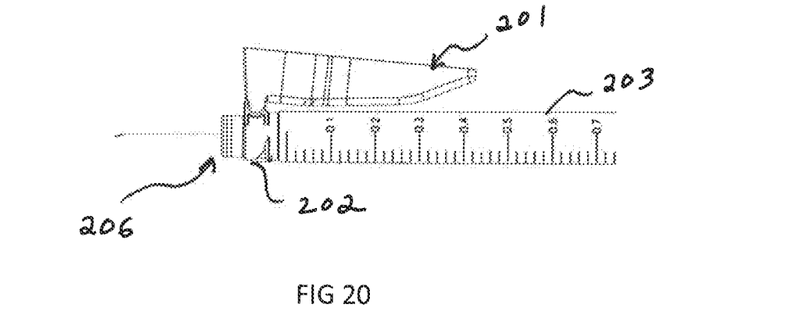
FIG. 20 is a side elevational view of the safety needle assembly shown in FIG. 19 attached to the Luer taper syringe.
Figure 21:
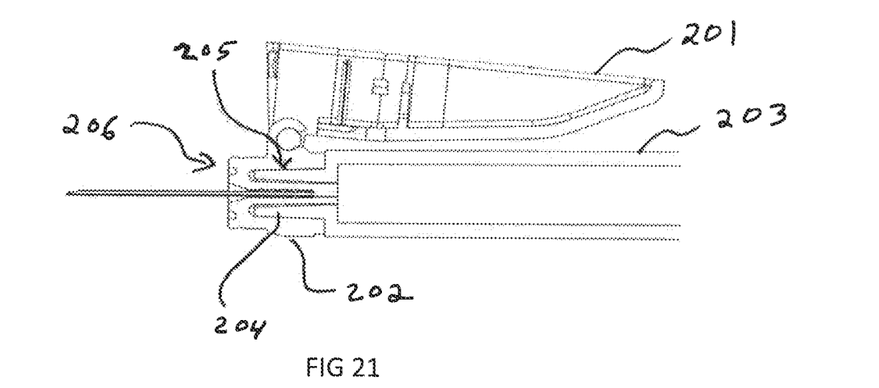
FIG. 21 is a cross-sectional view of assembled safety needle assembly and Luer taper syringe shown in FIG. 20.

Syringes normally come in standard volume capacities of 1, 2, 3, 5 and 10 mL for skin injections. For each size the length of the barrel is optimized based on the volume capacity and graduation of unit markings so that a user can accurately set the plunger to a dosage mark. Vaccine immunization typically requires a fraction of the smallest 1 ml version of syringe. The optimal syringe assembly of the current invention shown in FIG. 18 has been shortened to remove the unnecessary portion of the barrel and plunger rod that leads to more cost, manufacturing challenges (see barrel bow in the following section) and environmental waste. The smaller footprint of these shorter syringes will lead to additional cost savings including packaging, shipping and disposal. As shown in FIGS. 19, 20 and 21, a safety needle assembly 206 according to the current invention can alternatively be connected to a syringe barrel 203 using a Luer taper connection having a Female Luer taper in the cavity 205 of the hub 202 and a Male Luer taper on the barrel tip 204 of the syringe barrel 203. The Luer taper connection also provides a liquid tight seal between the internal hub cavity 205 and the external surface of the barrel tip 204.

Also note that the invention is suitable to self-contained syringes that do not require flexible packaging and instead use plastic caps to maintain sterility; re-use prevention (RUP) syringes with frangible plunger features that prevent re-use after an injection has been completed (as shown and described in EP0925083B1) and fixed dose auto-disable (AD) syringes with plunger locking element features that prevent re-use during and/or after movement of the plunger in the injection phase (as shown and described in U.S. Pat. No. 9,205,205).

The current invention also offers a low deadspace syringe with a protective guard design for either a healthcare provider or patient that can be easily and safety activated without the fear of the guard spinning or popping off during activation of the needle guard is beneficial and has been previously disclosed. Preventing unintended rotational movement of the needle guard during activation will remove the risk of a potential needle stick injury from occurring. The mounting of the needle guard to the needle hub adapter without allowing a means for rotation solves this potential issue. Having the needle hub permanently fixed to the barrel and the guard mounted directly to the hub also eliminates the hazard of a needle popping off the syringe distal tip if it had not been securely fastened by the user which can occur with Luer slip detachable type needles and syringes. Another benefit of the current invention is the low profile of the needle guard which allows for unobstructed visual viewing of the injection site and needle point position prior to injecting the patient. The low profile aids in reducing the likelihood the needle guard will snag onto loose clothing or bedding and get damaged or cause a needlestick injury. Another beneficial design feature is the distal end of needle guard (proximal to user before activation) having a slanted inverse ramp or curvature area 1202, as shown in FIGS. 11 and 13, which allows for guiding a user to place their fingertip between the underside of needle guard 101 and syringe barrel 103 to easily begin a single handed preferred activation method of the needle guard to the activated position. Low or even no waste-space is achieved and maintained with this design compared to a Luer needle hub and Luer syringe assembly.

The manufacturability of the current invention two pieces syringe barrel is also an improvement when compared to the one piece uni-body syringe barrel since the metal core-pin that creates the fluid chamber of the molded barrel is held in place by a support pin at the distal end that is much greater in diameter and stiffness within the mold which minimizes core shift (bending), the major contributing factor that causes syringe barrel bow in the molding process which is undesirable. "Bow" (banana shape) occurs when the proximal and distal ends of the barrel are out of alignment with the horizontal axis of the barrel cylinder, causing alignment issue in the assembly process. Alternatively, reducing the overall length of the barrel will also be beneficial towards molding the optimal straight concentric barrel.

Orienting needle bevel 915 relative to needle guard 101 is desirable in some injection practices like intradermal injections and this is easily achieved by the current invention during the manufacturing process when mounting the needle 911 in needle hub 102, thereby eliminating the user needing to rotate the needle guard during use.

The current invention also allows for color coding needle hub 102 by pigmenting the raw material to quickly and easily identifying the gauge of the needle cannula 911 is most desirable; having needle hub 102 molded separately from syringe barrel 103 as describe in this invention allows this improvement over integrally molded needle hub syringes. Integrally molded hub syringes cannot offer coloring options since the barrel is required to be made of a clear material so that the fluid content can easily be viewed.

Reading the syringe barrel graduation is also important to the medication preparation of the syringe by a healthcare worker. When manufacturing the current invention syringe barrel 103 and needle hub 102 with the needle guard 101, needle guard 101 may be positioned to best view the graduation. Another benefit to having the manufacturer position needle hub 102 and needle guard 101 is to align needle guard 101 with the finger flanges 107 of syringe 103 to minimize syringe packaging.

As will be recognized by those skilled in the art, the subject invention is not limited to these arrangements.

What is claimed is:

1. A safety syringe assembly comprising:
    a syringe barrel having an open proximal end with a first cylindrical portion extending distally therefrom, a barrel nozzle tip extending distally from the first cylindrical portion terminating at an open distal end, the barrel nozzle tip defining an outer diameter smaller than the first cylindrical portion, and a chamber between the open proximal end and the open distal end for retaining fluid, wherein the barrel nozzle tip includes an internal orifice extending proximally from the open distal end to a distal wall opening located at an interface between the barrel nozzle tip and the first cylindrical portion, the internal orifice defining a portion of the chamber, and an outer surface which encircles the internal orifice, the outer surface defining a radially-outwardly protruding locking ring spaced from the open distal end; and
    a needle assembly mountable to the syringe barrel, the needle assembly comprising:
        a hub having a proximal end, a distal end, and a conduit therethrough, the hub including a bulkhead at the distal end, a columnar cork extending proximally from the bulkhead to the proximal end, and an annular collar extending proximally from the bulkhead spaced from and encircling the cork, wherein, with the needle assembly mounted to the syringe barrel, the cork extends into the internal orifice of the barrel nozzle tip without extending through the distal wall opening, wherein the cork defines an outer surface dimensioned to interferingly engage, so as to be in sealing engagement, with the internal orifice of the barrel nozzle tip with the cork extending thereinto, wherein the collar defines an inwardly-facing locking trough, and, wherein the locking trough is configured to receivingly engage the locking ring defined on the barrel nozzle tip with the cork extending into the internal orifice of the barrel nozzle tip so as to maintain the sealing engagement between the cork and the internal orifice;
        a cannula having a proximal end, a distal end, and a lumen therethrough, wherein said cannula extends through said conduit along a substantial portion of the cork into proximity with the proximal end of the hub, and, wherein a first portion of said conduit extends from the proximal end of the hub to the proximal end of the cannula to define an open flow path between the proximal end of the hub and the proximal end of said cannula; and
        a guard rotatably mounted on said hub to rotate from an open position to a safety position, wherein said guard covers said distal end of said cannula when in said safety position,
    wherein the lumen of the cannula is in communication with the chamber of the syringe barrel, via the first portion of said conduit, with the needle assembly mounted to the syringe barrel.

2. The safety syringe assembly of claim 1, wherein said guard is rotatably mounted on said hub using a hinge.

3. The safety syringe assembly of claim 2, wherein said hinge is a pivot hinge having a pivot shaft on said guard that is received in a pivot mount clasp on said hub.

4. The safety syringe assembly of claim 3, wherein said guard can be user dependently parked between said open position and said safety position.

5. The safety syringe assembly of claim 2, wherein said hinge is a living hinge connecting said guard to said hub.

6. The safety syringe assembly of claim 1, wherein said guard has a tapered distal end to provide a gap between said guard and said syringe barrel when said guard is in said open position to facilitate activation by a user.

7. The safety syringe assembly of claim 1, further comprising a plunger rod having a distal end and a proximal end, said plunger rod being slidably mounted within said chamber of said syringe barrel.

8. The safety syringe assembly of claim 7, wherein a distally-facing annular stop wall extends between the barrel nozzle tip and the first cylindrical portion about the distal wall opening, and, wherein, with the needle assembly mounted to the syringe barrel, dead-space between said distal end of said cannula and said distal end of said plunger rod is no more than 10 μL when said distal end of said plunger rod abuts said stop wall.

9. The safety syringe assembly of claim 7, wherein a distally-facing annular stop wall extends between the barrel nozzle tip and the first cylindrical portion about the distal wall opening, wherein said distal end of said plunger rod includes a stopper, and, wherein dead-space between said distal end of said cannula and said stopper is no more than 10 μL when said stopper of said plunger rod abuts said stop wall.

10. The safety syringe assembly of claim 7, wherein said plunger rod includes a frangible feature to prevent re-use.

11. The safety syringe assembly of claim 7, wherein said syringe assembly includes an auto-disable plunger locking element feature to prevent re-use of the plunger rod.

12. The safety syringe assembly of claim 1, wherein said guard locks to said hub when in said safety position.

13. The safety syringe assembly of claim 1, wherein said guard traps said cannula within said guard when in said safety position.

14. The safety syringe assembly of claim 1, wherein said guard locks to said hub and traps said cannula within said guard when in said safety position.

15. The safety syringe assembly of claim 1, wherein said guard provides an audible click when entering said safety position.

16. The safety syringe assembly of claim 1, wherein said guard provides tactile feedback when entering said safety position.

17. The safety syringe assembly of claim 1, wherein said hub is permanently mounted to said syringe barrel.

18. The safety syringe assembly of claim 1, wherein said syringe assembly includes fixed-dose capability.

19. The safety syringe assembly of claim 1, wherein said syringe barrel includes gradations on an exterior surface and, with the needle assembly mounted to the syringe barrel, said guard is configured to not cover said gradations when in said open position.

* * * * *